United States Patent [19]

Uchiyama et al.

[11] Patent Number: 5,094,948

[45] Date of Patent: Mar. 10, 1992

[54] IMMOBILIZED FTF ENZYMES

[75] Inventors: Takao Uchiyama, Minoo; Akira Kamata; Hiroshi Kusano, both of Yokohama, all of Japan

[73] Assignee: Mitsubishi Kasei Corporation, Tokyo, Japan

[21] Appl. No.: 330,694

[22] Filed: Mar. 30, 1989

[30] Foreign Application Priority Data

Apr. 6, 1988 [JP] Japan .................................. 63-84833

[51] Int. Cl.$^5$ ..................... C12N 11/08; C12N 11/00; C12N 9/10
[52] U.S. Cl. .................................. 435/174; 435/180; 435/193; 435/830
[58] Field of Search ................ 435/180, 830, 193, 174

[56] References Cited

U.S. PATENT DOCUMENTS

| | | | |
|---|---|---|---|
| 4,170,696 | 10/1979 | Hirohara et al. | 435/180 |
| 4,239,854 | 12/1980 | Hirohara et al. | 521/31 |

FOREIGN PATENT DOCUMENTS

| | | |
|---|---|---|
| 0043169 | 1/1982 | European Pat. Off. . |
| 0132998 | 2/1985 | European Pat. Off. . |
| 0332108 | 9/1989 | European Pat. Off. . |
| 2082188 | 3/1982 | United Kingdom . |

OTHER PUBLICATIONS

Kawai et al., cited in Biol. Abstracts vol. 81: 61880 (1986).
Chemical Abstracts, vol. 79, No. 15, Oct. 15, 1973, p. 138, abstract No. 88677r, T. Uchiyama et al; "Purification and properties of . . ."
Chemical Abstracts, vol. 108, No. 17, Apr. 25, 1988, abstract no. 145962y, K. Haraguchi et al.; "Purification and Properties of Inulin . . ."
Chemical Abstracts, vol. 110, No. 11, Mar. 13, 1989, p. 318, abstract no. 91049b, M. Kawamura et al.; "Purification and Some Properties of Inulin . . ."

*Primary Examiner*—Jacqueline Stone
*Attorney, Agent, or Firm*—Oblon, Spivak, McClelland, Maier & Neustadt

[57] ABSTRACT

Disclosed herein is an immobilized enzyme inulin-D-fructotransferase carried in a specific anionic exchange resin with pores having a mode radius in the range of 75 to 2,000 angstroms. The immobilized enzyme of the present invention is effective in the production of DFA III from inulin.

4 Claims, No Drawings

IMMOBILIZED FTF ENZYMES

BACKGROUND OF THE INVENTION

1. Field of the Invention

The present invention relates to an immobilized enzyme which can advantageously be employed in the production of di-D-fructofuranose 2',1:2,3'-dianhydride, hereinafter referred to as "DFA III".

2. Description of the Prior Art

Inulin-D-fructotransferase (inulinase II), hereinafter abbreviated as "FTF", is an enzyme producing DFA III from inulin.

DFA III is a disaccharide having the structure in which two molecules of fructose are condensed with dehydration via 1,2'- and 2,3'-linkages, ad has been isolated and identified in 1931 by Jackson et al. *Bur. stand. J. Res.*, 6, 709 (1931). DFA III may notably be regarded as a low-calorie sweetener since it is not metabolized nor fermented in animal bodies and is expected to be utilized in various applications, including use for a diet food, in the future.

Various bacteria which may produce FTF have been known and include, for example, *Arthrobacter ureafaciens* 7116 (FERM P-1969), *Arthrobacter globiformis* C11-1 (FERM P-8748), *Arthrobacter aurescens* IFO 12136 (Uchiyama et al., 1975, the 48th congress of the Society of Japan Biochemistry), and *Pseudomonas fluorescens* No. 949 (Kuramoto et al., the congress of the Society of Japan Agricultural Chemistry, p. 654 (1987) and p. 112 (1988)).

The present inventors have also found that *Arthrobacter ilicis* MCI-2297 (FERM P-9893, also designated as FERM BP-2279 under the Budapest Treaty) can also produce FTF Japanese Patent Application No. 53164/1988; Uchiyama et al., the congress of the Society of Japan Agricultural Chemistry, p. 296 (1988).

In conventional enzymic reactions utilizing such enzymes in aqueous solutions, modification or removal of the enzymes will be required in order to industrially collect desired products after reaction. Thus, the enzymes should be discarded every reaction even though they are still active, resulting in economical disadvantages.

If an attempt is made to recover the enzymes, then some treatment such as ultrafiltration will necessarily be done which requires a lot of equipments and time to separate the enzymes from the reaction mixture. Thus, this is also disadvantageous economically.

SUMMARY OF THE INVENTION

The present inventors have made great efforts to overcome the above-mentioned disadvantages and investigated various methods which could be industrially advantageous. It has surprisingly been found that an immobilized enzyme (FTF) in which the enzyme is preliminarily carried in a particular anionic exchange resin may not only be employed with economical advantages (e.g., it can be recycled), but also it may provide a higher amount of enzyme adsorbed, enzyme activity and/or binding force between the enzyme and the carrier resin. In addition, the enzyme carried in such a resin shows a very high and stable activity.

It is a primary object of the present invention, accordingly, to provide an immobilized FTF with a large amount of enzyme adsorbed and a high enzyme activity.

According to the present invention, this object and other ones which will be apparent from the following description of the invention can be attained by providing an immobilized FTF enzyme in which FTF is carried in an anionic exchange resin with pores having a mode radius as defined clearly hereinbelow of 75 to 2,000 angstroms.

DESCRIPTION OF THE INVENTION

The present invention will hereinafter be described in detail.

The enzyme FTF which is carried or supported in the specific anionic exchange resin according to the present invention may be any FTF enzyme which can catalyze the reaction for producing DFA III from inulin.

Such an enzyme may be produced by various bacteria, including those belonging to the genus Arthrobacter such as, for example, *Arthrobacter ureafaciens*, *Arthrobacter globiformis*, *Arthrobacter aurescens* and *Arthrobacter ilicis*; and those belonging to the genus Pseudomonas such as *Pseudomonas fluorescens*. Illustrative examples of bacteria which can produce such an enzyme, FTF, may include, for example, *Arthrobacter ureafaciens* 7116 (FERM P-1969), *Arthrobacter globiformis* C11-1 (FERM P-8748), *Arthrobacter aurescens* IFO 12136, *Arthrobacter ilicis* MCI-2297 (FERM BP-2279),and *Pseudomonas fluorescens* No. 949Kuramoto et al., the congress of the Society of Japan Agricultural Chemistry, p. 654 (1987) and p. 112 (1988).

In producing the enzyme FTF, such a bacterium as above-mentioned may be cultured in any corresponding manner. When enzymes produced are secreted in the culture medium, they may be separated from the cells by centrifugation, filter press, and the like method. When the produced enzymes are remained within the cells, various known methods may be employed to obtain FTF; for instance, mechanical methods such as ultrasonication and pressing can be used, or the autolysis in which the cells are spontaneously disintegrated by their cytolytic enzymes by themselves can be utilized.

Anionic exchange resins which may be used herein should have pores therein with a mode radius in the range of 75 to 2,000 angstroms, preferably 75 to 1,000 angstroms.

The "mode radius" used herein means the most frequent value in radii of all pores present in the anionic exchange resin used.

In preferred anionic exchange resins for the present invention, the total volume of pores having a radius in the range of 75 to 3,000 angstroms (hereinafter sometimes referred to as "pore volume") is at least 0.1 ml/g, especially in the range of 0.3 to 2.5 ml/g, and the specific surface area of resin particles is at least 0.1 $m^2/g$, especially in the range of 10 to 100 $m^2/g$. Such porous resins can well adsorb and carry FTF and thus be advantageously employed in the present invention.

The physical properties, i.e., specific surface area and pore volume, of the anionic exchange resin used in preparing the present immobilized FTF are measured for a sample of the porous anionic exchange resin dried under a reduced pressure of a few mmHg at 50° C. for 10 hours, according to the B.E.T. method and mercury porosimetry (Autopore 200 from MICROMETRIC Company), respectively.

The porous anionic exchange resins used herein may be manufactured by various known methods. Generally, base materials for the ion exchange resins may be prepared by copolymerizing at least one monovinyl monomers and at least on polyvinyl monomers. Monovinyl monomers which can be preferably used herein may include aromatic monovinyl compounds, such as styrene, and aliphatic monomers, such as acrylic and methacrylic acids or their esters. Preferred polyvinyl monomers may include aromatic divinyl compounds, such as divinylbenzene, and aliphatic compounds, such as ethylene glycol dimethacrylate.

To render such resinous base materials porous, the aforementioned monomers may be polymerized in the presence of a substance which can be removed later by solvent extraction and does not interfere in the polymerization reaction, for example polystyrene, followed by treating the resulting resin with an appropriate solvent to extract the substance such as polystyrene after reaction.

Physical properties of the porous resins, such as the specific surface area, the pore size, and the total volume of pores having a radius of 75 angstroms or more, may be varied by suitably selecting the conditions for the preparation of the resins. It is difficult to uniquely determine any relationship between the physical properties and the conditions for the preparation of the resins. For example, when styrene and divinylbenzene are used to prepare the base material in the above described method, larger amounts of divinylbenzene used will generally tend to yield higher porosities, i.e., larger specific surface areas, pore volumes and/or pore radii; and larger amounts of polystyrene will also tend to result in larger pore volumes or sizes.

Anionic exchange groups may be introduced into the resin by introducing chloromethyl groups into the base resinous material, followed by treating it with various amines, including aliphatic amines such as trimethylamine, dimethylethanolamine, ethylenediamine, diethylenetetramine, triethylenetetramine and the like and cyclic amines such as pyrrolidine, morpholine and piperidine, preferably with aliphatic amines. Alternatively, a vinyl monomer having a highly reactive functional group, for example glycidyl (meth)acrylate or vinylbenzyl glycidyl ether, may previously be copolymerized in the synthesis of the base resinous material followed by adding various amines to the glycidyl group while causing the ring-opening reaction thereof to proceed, under basic conditions. By suitably selecting the properties of the aforementioned base resinous material and the nature of amine used, preferred anionic exchange resins can be obtained in which FTF enzyme carried therein will exhibit a high activity.

It may also be preferred that the degree of crosslinking in the base resin is suitably selected by taking into consideration the above described factors such as the pore properties of the resin and the nature of anionic exchange resin used, since higher degrees of crosslinking tend to decrease both the amount and activity of enzyme adsorbed. Thus, when such a resin is prepared by copolymerizing styrene with a crosslinkable monomer such as divinylbenzene, the latter is generally used in an amount of 50% by mole or less, preferably 25% by mole or less.

Also, acrylic resins based on poly(meth)acrylic acid which may be prepared in conventional manners can be employed herein as the porous resin substrate as appropriate.

In the present invention, the porous anionic exchange resins generally have a particle size in the range of about 20 to 400 mesh. The smaller the particle size is, the higher the enzyme activity will tend to become.

The FTF enzyme may be adsorbed by the aforementioned anionic exchange resin according to any of generally known methods for treating ion exchange resins. Most conveniently, the ion exchange resin may be immersed into an aqueous FTF solution obtained by removing cells from a culture of such a bacterium as mentioned above, stirred if necessary, and after an appropriate adsorption period, removed out and washed with water. The aqueous FTF solution usually has a pH in the range of 3.0 to 10.0. The temperature at which the adsorption operation is carried out is in the range of from 0° to 60° C. The period of time required for the adsorption is about 1 to 20 hours.

The aforementioned anionic exchange resin carrier may be employed in the form of various salts. For example, the ion exchange resin may be treated with an aqueous solution of sulfuric acid, hydrochloric acid, sodium hydroxide, phosphoric acid, or acetic acid to produce $HSO_4^-$, $SO_4^{2-}$, $Cl^-$, $OH^-$, $HPO_4^-$, $PO_4^{2-}$, or $CH_3COO^-$ salt form, preferably $SO_4^{2-}$, $Cl^-$, $OH^-$, or $PO_4^{2-}$ salt form. To the carriers of these salt forms, FTF can be effectively adsorbed.

The amount of enzyme adsorbed by the carrier is usually in the range of 0.05 to 30 mg protein, preferably 0.1 to 10 mg protein, per ml resin in wet state.

Although the mechanism by which FTF is adsorbed by the anionic exchange resin and the mechanism through which FTF effects its activity according to the present invention have not fully been understood, it may be believed that both the physical adsorption by the resin pores and any chemical binding force formed between the anionic exchange groups and FTF may synergistically involve in these mechanisms. This may also be deduced from the fact that conventional gel-like ion exchange resins having a small specific surface area and a low volume of pores of 75 angstroms or more in radius can hardly adsorb FTF, and that, on the other hand, the amount of FTF adsorbed is still small and the activity thereof is also low with porous resins having a large specific surface area and a high volume of pores of 75 angstroms or more in radius but having no anionic exchange group introduced thereinto.

The anionic exchange resins used in the present invention may swell in an aqueous solution to form a larger network than in the dry state. However, those resins having larger pore radii and pore volumes in the dry state will result in better adsorption and activity of FTF.

The thus obtained insolubilized enzymes remain the high activity of FTF. In addition, the immobilized FTF enzymes according to the present invention can be used for a long period of time without significant decrease of the enzyme activity. Further, the enzyme is not released out of the carrier. Therefore, the enzyme reaction can advantageously be effected in an industrial scale. When the immobilized FTF enzymes of the present invention are utilized industrially, any reactor of packed, agitated or other type can be employed.

One of the advantages of the present immobilized FTF enzymes is that in such immobilized enzyme-resins having a reduced activity after long use, the FTF enzyme can be readily released from the resin which is thus regenerated, by simply treating the immobilized enzyme-resin with an aqueous sodium or potassium chloride solution. After the regeneration, fresh FTF may be adsorbed and carried by the regenerated ion exchange resin to reproduce an immobilized FTF enzyme-resin having a high activity.

EXAMPLES

The present invention will be further illustrated by the following examples. It should be understood that the invention is not limited to these examples unless departing from the scope thereof as defined in the attached claims.

EXAMPLE 1

*Arthrobacter ilicis* MCI 2297 (FERM BP-2279) was cultured in a 5 liter Sakaguchi flask containing 500 ml of a medium as specified hereinbelow at 30° C. for 24 hours.

| | |
|---|---|
| inulin | 50 g |
| sodium nitrate | 2 g |
| magnesium sulfate heptahydrate | 0.5 g |
| potassium chloride | 0.5 g |
| potassium dihydrogenphosphate | 0.5 g |
| iron (III) chloride | 0.001 g |
| yeast extract | 0.2 g |
| water | 1 liter |

After culture, cells were removed by centrifugation to yield an FTF solution having an activity of 21U.

Then, 150 ml of the enzyme solution was added to 1 ml of a wet ion exchange resin having physical properties as shown in Table 1 below and agitated with shaking at 30° C. for 10 hours causing the resin to adsorb the enzyme. Thus, an immobilized FTF solution according to the present invention was obtained.

The immobilized FTF-resin was washed with water and then twice with 10 ml of a reaction mixture (10% inulin, 0.05M phosphate buffer, pH 6.0). To the washed resin, 100 ml of the reaction mixture was added, and the reaction was conducted with shaking and agitating at 30° C. for one hour.

The activity of the immobilized FTF enzyme-resin as measured by high performance liquid chromatography is shown in Table 1.

As shown in Table 1, 3.29 g of DFA III was produced in the reaction mixture.

Thereafter, the immobilized enzyme-resin was twice washed with 10 ml fresh reaction mixture, and 100 ml fresh reaction mixture was again added. After similar reaction for one hour, 3.01 g of DFA III was produced in the reaction mixture. Similarly, the third reaction was conducted to produce 3.00 g of DFA III.

The determination of enzyme activities and analysis of DFA III was herein conducted according to the following methods:

(1) Measurement of enzyme activity

Inulin (10 g) was dissolved in 90 ml of 0.05M phosphate buffer (pH 6.0) and the total volume was adjusted to 100 ml. An enzyme solution (1 ml) was added to the thus prepared inulin solution (2 ml) and reaction was conducted with shaking at 30° C. for one hour. After reaction, 3 ml of methanol was added to the reaction mixture and water added to make the volume to 30 ml. The produced DFA III was then analyzed by high performance liquid chromatography. An enzyme activity producing 1 g of DFA III per hour per liter of enzyme solution is expressed as 1U (unit).

(2) Analysis of DFA III produced

DFA III was analyzed by high performance liquid chromatography using CK08S column manufactured by Mitsubishi Kasei Corporation, Japan, water as eluent at a flow rate of 1 ml per minute, and a differential refractometer as detector.

EXAMPLES 2 TO 9 AND COMPARATIVE EXAMPLES 1 TO 7

Various immobilized FTF-resins were prepared by repeating the procedures of Example 1 except that the nature and ion-type of the exchange resins used were changed as shown in Table 1.

Activities of the resulting immobilized FTF-resins are also shown in Table 1.

In Table 1, the units employed are as followed 1) mode radii expressed in angstroms, 2) volumes of pores having a radius of 75 to 3,000 angstroms in ml/g, 3) specific surface areas in $m^2/g$, and 4) activities of immobilized FTF enzymes in weights (g) of DFA III produced per 100 ml per ml of resin per hour.

TABLE 1

| | Properties of Ion Exchange Resin | | | | | Activity of |
|---|---|---|---|---|---|---|
| | Anionic Exchange Group Type | Mode Radius | Pore Volume | Specific Surface Area | Salt Form | Immobilized FTF Enzyme |
| Example | | | | | | |
| 1 | Dimethylethanolammonium-; (a) | 660[1] | 0.9[2] | 24[3] | $OH^-$ | 3.29[4] |
| 2 | Dimethylethanolammonium-; (a) | 660 | 0.9 | 24 | $Cl^-$ | 3.00 |
| 3 | Dimethylethanolammonium-; (a) | 660 | 0.9 | 24 | $PO_4^{2-}$ | 2.92 |
| 4 | Trimethylammonium-; (b) | 620 | 0.9 | 23 | $PO_4^{2-}$ | 2.52 |
| 5 | Trimethylammonium-; (c) | 497 | 0.8 | 44 | $PO_4^{2-}$ | 1.02 |
| 6 | Dimethylamino-; (d) | 450 | 0.5 | 15 | $PO_4^{2-}$ | 1.22 |
| 7 | Dimethylamino-; (e) | 340 | 1.1 | 52 | $PO_4^{2-}$ | 2.96 |
| 8 | Hexamethylenediamine-; (f) | 340 | 1.1 | 52 | $PO_4^{2-}$ | 2.23 |
| 9 | Hexamethylenediamine-; (g) | 83 | 0.4 | 64 | $PO_4^{2-}$ | 1.77 |
| Comparative Example | | | | | | |
| 1 | Hexamethylenediamine-; (h) | 2200 | 1.7 | 21 | $PO_4^{2-}$ | 0 |
| 2 | No exchange group; (i) | 300 | 1.2 | 510 | — | 0.2 |
| 3 | No exchange group; (j) | 1000 | 1.2 | 40 | — | 0.1 |
| 4 | No exchange group; (k) | 340 | 1.1 | 52 | — | 0.2 |
| 5 | Sulfonic Acid-Type Cationic Exchange Resin; (m) | 290 | 0.2 | 17 | $Na^+$ | 0 |
| 6 | Dimethylethanolammonium-; (n) | ≦30 | <0.1 | <0.1 | $PO_4^{2-}$ | 0 |
| 7 | Dimethylethanolammonium-; (p) | ≦30 | <0.1 | <0.1 | $PO_4^{2-}$ | 0.3 |

In Table 1, the bracketed letter (a) denotes DIAION HPA 75, (b) DIAION HPA 25, (c) Amberlite IRA 904 commercially available from Rohm & Haas Co., (d) DIAION WA 30, (e) SEPHABEADS FPDA 13, (f) SEPHABEADS FPHA 13, (g) SEPHABEADS FPHA 20, (h) SEPHABEADS FPHA 05, (i) DIAION HP 20, (j) porous adsorbent MPX-01, (k) SEPHABEADS FP-HG 13, (m) DIAION HPK 25, (n) DIAION SA 21 A, and (p) DIAION PA 406; these resins being commercially available from Mitsubishi Kasei Corporation, Japan, unless otherwise specified.

EXAMPLE 10

Another immobilized FTF-resin of the present invention was prepared by repeating the procedures of Example 1 except that the strain used was *Arthrobacter aurescens* IFO 12136. (The enzyme solution obtained by the culture of this strain had an activity of 7.4U.) The activity of the resulting immobilized enzyme is shown in Table 2.

EXAMPLE AND COMPARATIVE EXAMPLES 8 AND 9

Some other immobilized FTF-resins were prepared by repeating the procedures of Example 10 except that the nature of ion exchange group of the exchange resins used were changed as shown in Table 2.

The activities of the resulting immobilized FTF enzymes are also shown in Table 2.

As seen from the foregoing examples, the enzyme carried by the immobilized enzyme-resins according to the present invention exhibits its satisfactorily high activity permitting higher production of DFA III. In addition, it will be industrially advantageous that the immobilized enzymes of the present invention can repeatedly be employed to produce DFA III.

What is claimed is:

1. An immobilized enzyme in which an inulin-D-fructotransferase enzyme, derived from a culture of *Arthrobacter ilicis*, is immobilized onto an ionic exchange resin with pores having a mode radius in the range of 75 to 2,000 angstroms, wherein said ionic exchange resin is an anionic exchange resin having dimethylethanolammonium, trimethylammonium, dimethylamino, or hexamethylenediamine groups.

2. The immobilized enzyme of claim 1, wherein the volume of pores having a radius of 75 to 2,000 angstroms is at least 0.1 ml/g resin.

3. The immobilized enzyme of claim 2, wherein the anionic exchange resin has a specific surface area of at least 0.1 m²/g.

4. The immobilized enzyme of claim 1 wherein, said inulin-D-fructotransferase is derived from a culture of *Arthrobacter ilicis* MCI 2297 (FERM BP-2279).

* * * * *

TABLE 2

| | Properties of Ion Exchange Resin | | | | | Activity of Immobilized FTF Enzyme |
|---|---|---|---|---|---|---|
| | Anionic Exchange Group Type | Mode Radius | Pore Volume | Specific Surface Area | Salt Form | |
| Example | | | | | | |
| 10 | Hexamethylenediamine-; (f) | 340[1] | 1.1[2] | 52[3] | $PO_4^{2-}$ | 1.0[4] |
| 11 | Dimethylethanolammonium-; (a) | 660 | 0.9 | 24 | $PO_4^{2-}$ | 1.1 |
| Comparative Example | | | | | | |
| 8 | Hexamethylenediamine-; (h) | 2200 | 1.7 | 21 | $PO_4^{2-}$ | 0 |
| 9 | Dimethylethanolammonium-; (n) | ≦30 | <0.1 | <0.1 | $PO_4^{2-}$ | 0 |

In Table 2, units [1] to [4] and resin types (a), (f), (h) and (n) are as defined in Table 1.